US011026826B2

(12) United States Patent
Dicesare et al.

(10) Patent No.: US 11,026,826 B2
(45) Date of Patent: Jun. 8, 2021

(54) FLANGED GASTROINTESTINAL DEVICES AND METHODS OF USE THEREOF

(71) Applicant: GI Dynamics, Inc., Boston, MA (US)

(72) Inventors: Paul Dicesare, Easton, CT (US); Jeffrey P. Radziunas, Wallingford, CT (US); Ronald L. Green, Bethel, CT (US); Dominick L. Mastri, Bridgeport, CT (US); Scott Schorer, Duxbury, MA (US); Nicholas Williams, Sydney (AU)

(73) Assignee: GI Dynamics, Inc., Boston, MA (US)

( * ) Notice: Subject to any disclaimer, the term of this patent is extended or adjusted under 35 U.S.C. 154(b) by 198 days.

(21) Appl. No.: 16/073,661

(22) PCT Filed: Jan. 30, 2017

(86) PCT No.: PCT/US2017/015650
§ 371 (c)(1),
(2) Date: Jul. 27, 2018

(87) PCT Pub. No.: WO2017/132673
PCT Pub. Date: Aug. 3, 2017

(65) Prior Publication Data
US 2019/0029859 A1  Jan. 31, 2019

Related U.S. Application Data

(60) Provisional application No. 62/289,100, filed on Jan. 29, 2016.

(51) Int. Cl.
*A61F 5/00* (2006.01)
*A61F 2/04* (2013.01)
(Continued)

(52) U.S. Cl.
CPC .............. *A61F 5/0076* (2013.01); *A61F 2/04* (2013.01); *A61F 5/00* (2013.01); *A61F 5/0089* (2013.01);
(Continued)

(58) Field of Classification Search
CPC ........ A61F 5/0076; A61F 5/00; A61F 5/0089; A61F 2/04; A61F 2005/045; A61M 29/00; A61M 29/02
See application file for complete search history.

(56) References Cited

U.S. PATENT DOCUMENTS 7,025,791 B2    4/2006  Levine et al.
7,122,058 B2   10/2006  Levine et al.
(Continued)

FOREIGN PATENT DOCUMENTS

| EP | 2484316 A2 | 8/2012 |
| WO | WO-2011/099940 A1 | 8/2011 |
| WO | WO-2013/023675 A1 | 2/2013 |

OTHER PUBLICATIONS

Extended European Search Report for European Application No. 17745090.5, dated Oct. 24, 2019 (7 pages).
(Continued)

*Primary Examiner* — Ariana Zimbouski
(74) *Attorney, Agent, or Firm* — Clark & Elbing LLP

(57) ABSTRACT

The present invention provides gastrointestinal devices for limiting transfer and contact of material across luminal walls along a segment of the gastrointestinal tract (e.g., at the duodenum and/or upper jejunum). Devices of the invention include a gastrointestinal sleeve, an anchor, and a flange for attachment to a luminal wall proximal to the pyloric orifice. The invention also provides methods of use associated with such gastrointestinal devices, including methods for delivery, removal, and treatment of metabolic disorders, such as
(Continued)

type 2 diabetes, non-alcoholic steatohepatitis, non-alcoholic fatty liver disease, obesity, and related comorbidities thereof by implanting gastrointestinal devices.

14 Claims, 7 Drawing Sheets

(51) Int. Cl.
*A61M 29/00* (2006.01)
*A61M 29/02* (2006.01)
(52) U.S. Cl.
CPC ............ *A61M 29/00* (2013.01); *A61M 29/02* (2013.01); *A61F 2002/045* (2013.01)

(56) References Cited

U.S. PATENT DOCUMENTS

| | | | |
|---|---|---|---|
| 7,476,256 B2 | 1/2009 | Meade et al. | |
| 7,608,114 B2 | 10/2009 | Levine et al. | |
| 7,678,068 B2 | 3/2010 | Levine et al. | |
| 7,682,330 B2 | 3/2010 | Meade et al. | |
| 7,695,446 B2 | 4/2010 | Levine et al. | |
| 7,766,973 B2 | 8/2010 | Levine et al. | |
| 7,771,382 B2 | 8/2010 | Levine et al. | |
| 7,815,589 B2 | 10/2010 | Meade et al. | |
| 7,815,591 B2 | 10/2010 | Levine et al. | |
| 7,837,643 B2 | 11/2010 | Levine et al. | |
| 7,976,488 B2 | 7/2011 | Levine et al. | |
| 7,981,163 B2 | 7/2011 | Meade et al. | |
| 8,057,420 B2 * | 11/2011 | Meade | A61F 2/04 604/8 |
| 8,137,301 B2 | 3/2012 | Levine et al. | |
| 8,162,871 B2 | 4/2012 | Levine et al. | |
| 8,303,669 B2 | 11/2012 | Meade et al. | |
| 8,425,451 B2 | 4/2013 | Levine et al. | |
| 8,628,583 B2 | 1/2014 | Meade et al. | |
| 8,771,219 B2 | 7/2014 | Meade et al. | |
| 8,834,405 B2 | 9/2014 | Meade et al. | |
| 9,084,699 B2 | 7/2015 | Sue et al. | |
| 9,095,416 B2 | 8/2015 | Meade et al. | |
| 9,155,609 B2 | 10/2015 | Levine et al. | |
| 9,237,944 B2 | 1/2016 | Meade et al. | |
| 2008/0255587 A1 * | 10/2008 | Cully | A61F 5/0089 606/139 |
| 2012/0065571 A1 * | 3/2012 | Thompson | A61F 5/0076 604/8 |
| 2012/0184967 A1 | 7/2012 | Levine et al. | |
| 2013/0281911 A1 | 10/2013 | Babkes et al. | |
| 2014/0018719 A1 * | 1/2014 | Chamorro, III | A61F 2/04 604/8 |
| 2017/0312112 A1 * | 11/2017 | Gobel | A61F 5/0043 |

OTHER PUBLICATIONS

International Search Report and Written Opinion for International Application No. PCT/US2017/015650, dated Apr. 7, 2017 (13 pages).

* cited by examiner

Endoscopic suturing device, end effector similar to Wilson-Cook model

Endoscopic suture cutting scissors, end effector similar to MSI model W26002, 3mm miniature hook scissors

FLANGED GASTROINTESTINAL DEVICES AND METHODS OF USE THEREOF

BACKGROUND OF THE INVENTION

According to the Center for Disease Control, 9.3% of the population of the United States has been diagnosed with type 2 diabetes or is predicted to develop type 2 diabetes, over half of whom are clinically obese. Type 2 diabetes and obesity can be broadly characterized as metabolic disorders, which often lead to life-threatening co-morbidities including non-alcoholic steatohepatitis (NASH), non-alcoholic fatty liver disease (NAFLD), hypertension, coronary artery disease, hypercholesteremia, sleep apnea, and pulmonary hypertension.

Patients suffering from metabolic diseases typically have an aberrant physiological response to ingested food after a meal. In particular, inadequate secretion of insulin has been associated with development of metabolic disorders such as type 2 diabetes. This blunted insulin response is caused by a loss or reduction of the "incretin effect," the gut-dependent secretion of incretins (e.g., hormones such as glucagon-like peptide-1 (GLP-1) and glucose-dependent insulinotropic polypeptide (GIP)). Thus, the modulation of signaling pathways in the gastrointestinal tract is emerging as a promising approach for treating metabolic disorders, such as type 2 diabetes, obesity, and related comorbidities.

Many conventional treatments involve surgical modification of gastrointestinal anatomy. Such procedures include, for example, gastric remodeling and gastric bypass. Unfortunately, the morbidity rate for surgical procedures is alarmingly high, with 11% of cases requiring surgical intervention for correction. Early small bowel obstruction has been estimated to occur at a rate of between 2-6% in these surgeries, and mortality rates are reported to be approximately 0.5-1.5%, and are most likely much higher. While invasive surgery seems to be effective when successfully performed, the associated complication rates are unacceptably high. Laparoscopic techniques adapted to these procedures provide fewer surgical complications but continue to expose these patients to high operative risk in addition to requiring an enormous level of skill by the surgeon.

Thus, there is a need in the field for minimally invasive procedures for treatment of metabolic disorders, such as type 2 diabetes, NASH, NAFLD, obesity, and related comorbidities thereof, by modulating physiological responses to ingested food.

SUMMARY OF THE INVENTION

The present invention provides gastrointestinal devices and methods for treatment of metabolic disorders. In one aspect, the invention features a gastrointestinal device having a sleeve configured to carry fluid (e.g., liquid or semi-solid material, for example, chyme and digestive secretions) from its proximal end to its distal end, wherein its proximal end is configured to be positioned at or proximal to a subject's pyloric orifice and its distal end is configured to be positioned at the subject's duodenum and/or proximal jejunum (e.g., distal to the duodenum). In some embodiments, the gastrointestinal device additionally features an anchor connected to the sleeve and configured to be retained within a duodenal bulb. At its proximal end, the gastrointestinal device also includes a flange configured to resist distal migration of the gastrointestinal device.

In some embodiments, the anchor of the gastrointestinal device is not configured to puncture a gastrointestinal wall (e.g., the anchor is barbless).

The anchor may be configured to exert an outward radial force on a duodenal bulb lumen. For example, the outward radial force can be at least 0.1 Newtons (N) at an anchor diameter of 25 millimeters (mm)(e.g., at least 0.11 N, at least 0.12 N, at least 0.13 N, at least 0.14 N, at least 0.15 N, at least 0.2 N, at least 0.25 N, at least 0.3 N, at least 0.35 N, at least 0.4 N, at least 0.45 N, at least 0.5 N, at least 0.6 N, at least 0.7 N, at least 0.8 N, at least 0.9 N, at least 1.0 N, or more, e.g., from 0.1 N to 0.2 N, from 0.2 N to 0.3 N, from 0.3 N to 0.4 N, from 0.4 N to 0.5 N, or more at an anchor diameter of 25 mm). In some embodiments, the anchor of the gastrointestinal device has an average spring rate of at least 10 N per meter (N/m)(e.g., at least 10 N/m, at least 11 N/m, at least 12 N/m, at least 13 N/m, at least 14 N/m, at least 15 N/m, at least 20 N/m, at least 25 N/m, at least 30 N/m, at least 35 N/m, at least 40 N/m, or more, e.g., from 10 N/m to 15 N/m, from 15 N/m to 20 N/m, from 20 N/m to 25 N/m, from 25 N/m to 30 N/m, or more) over its range of motion.

The anchor of the gastrointestinal device can be connected to the sleeve at a sleeve-coupling interface by a coupling liner (e.g., made of the same or a different material than the sleeve). In some embodiments, the maximum diameter of the sleeve at the sleeve-coupling interface is less than the relaxed diameter of the anchor. In some cases, the anchor is configured to exert an outward radial force on the sleeve at the sleeve-coupling interface. In some embodiments, the outward radial force on the sleeve at the sleeve-coupling interface is configured to maintain the sleeve in an open configuration (e.g., wholly or partially open) at the sleeve-coupling interface. The sleeve-coupling interface may be at or distal to the distal-most end of the anchor. Additionally or alternatively, the sleeve-coupling interface may be from 1-6 inches distal to the flange and/or the proximal end of the sleeve.

In some embodiments of the invention, the anchor of the gastrointestinal device is a wave anchor, and the proximal edge of the coupling liner matches the shape of the wave anchor (e.g., to form a "tulip" shape). In some embodiments, the wave anchor is a five-node sinusoidal wave anchor. The wave anchor can have a length from about 0.5 to about 2 inches (e.g., about 0.5 inches, about 0.6 inches, about 0.7 inches, about 0.8 inches, about 0.9 inches, about 1 inch, about 1.1 inches, about 1.2 inches, about 1.3 inches, about 1.4 inches, about 1.5 inches, about 1.6 inches, about 1.7 inches, about 1.8 inches, about 1.9 inches, or about 2 inches). In some embodiments, the wave anchor has a compressive elastic deformation diameter of 12 mm or less (e.g., from 5 to 12 mm, from 7 to 11 mm, or from 8 to 10 mm, e.g., about 11 mm, about 10 mm, about 9 mm, about 8 mm, about 7 mm, about 6 mm, about 5 mm, about 4 mm, about 3 mm, about 2 mm, or about 1 mm). In some cases, the wave anchor has a compressive elastic deformation of 30% or less (e.g., from 1% to 10%, from 10% to 20%, or from 20% to 30%, e.g., about 5%, about 10%, about 15%, about 20%, or about 25%). In some embodiments, the relaxed diameter of the wave anchor is at least 40 mm (e.g., at least 45 mm, at least 50 mm, at least 55 mm, at least 60 mm, at least 65 mm, or more).

The gastrointestinal device can optionally include a drawstring connected to the anchor (e.g., the wave anchor), wherein the drawstring is configured to exert an inward radial force on a proximal portion of the wave anchor when the drawstring is pulled proximally. The drawstring enables a practitioner to collapse the anchor for removal of the device.

In some embodiments, the flange is directly connected to the proximal end of the sleeve. For example, the flange can be integrally formed with the proximal end of the sleeve. In some embodiments, the flange and the sleeve are made from a polymeric liner, wherein all or a portion of the sleeve is thinner than the polymeric liner of the flange. The polymeric liner can be selected, foe example, from the group consisting of polytetrafluoroethylene (PTFE), expanded PTFE (ePTFE), fluorinated ethylene propylene (FEP), perfluoroalkoxy (PFA), ethylene tetrafluoroethylene (ETFE), and polyvinylidene fluoride (PVDF).

In some embodiments, the flange is a circular flange. For example, the flange extends around the full circumference of the proximal end of the sleeve and has a substantially constant radius. In some embodiments, a maximum outer diameter of the flange is at least 100% greater than a diameter of the sleeve (e.g., about 100% greater than, about 110% greater than, about 120% greater than, about 130% greater than, about 140% greater than, about 150% greater than, about 200% greater than, about 250% greater than, about 300% greater than, any percentage between these numbers, or more, e.g., from 100% to 10,000%, from 200% to 5,000%, from 300% to 2,000%, from 400% to 1,000%, from 500% to 800%, or more).

In some embodiments, the diameter of the sleeve is substantially constant along its length and may have a length of at least 40 cm (e.g., about 40 cm, about 45 cm, about 50 cm, about 55 cm, about 60 cm, about 65 cm, about 70 cm, about 75 cm, about 80 cm, about 85 cm, about 90 cm, about 95 cm, about 100 cm, about 110 cm, about 120 cm, about 130 cm, about 140 cm, or about 150 cm). The sleeve may also be substantially non-compliant and/or may have a coefficient of friction (e.g., a static coefficient of friction or a kinetic coefficient of friction (e.g., on its inner surface, e.g., in a longitudinal direction, e.g., a sliding coefficient of friction determining the rate of chyme passage through the sleeve)) of 0.3 or less (e.g., about 0.29, about 0.28, about 0.27, about 0.26, about 0.25, about 0.24, about 0.23, about 0.22, about 0.21, about 0.2, about 0.19, about 0.18, about 0.17, about 0.16, about 0.15, about 0.14, about 0.13, about 0.12, about 0.11, about 0.1, or less). In some embodiments, the sleeve includes an eversion-resistant element distal to the sleeve-coupling interface.

In another aspect, the invention provides a method of implanting the gastrointestinal device of any of the preceding embodiments by attaching the flange to a proximally oriented luminal surface proximal to the pyloric orifice (e.g., at a proximal surface of the pyloric sphincter or the antrum of the stomach).

In a further aspect, the invention provides a method of treating a metabolic disorder by implanting the gastrointestinal device of any of the preceding embodiments by attaching the flange to a proximally oriented luminal surface proximal to the pyloric orifice (e.g., at a proximal surface of the pyloric sphincter or the antrum of the stomach). In some embodiments, the metabolic disorder is selected from the group consisting of type 2 diabetes, non-alcoholic steatohepatitis (NASH), non-alcoholic fatty liver disease (NAFLD), obesity, or a related comorbidity thereof.

In some embodiments of either of the preceding methods, the attaching of the anchor and/or flange to the gastrointestinal tract is performed endoscopically and/or includes transmission of a distal force from an attachment element to the proximally oriented luminal surface. In some embodiments, the attaching of the anchor and/or flange to the gastrointestinal tract involves puncturing a gastrointestinal wall. In some embodiments, the attachment element includes a suture or a staple or other fixation device that crosses through both the cross section of the flange and into and or through the adjacent anatomical feature in order to provide semi-permanent fixation (e.g., fixation for 1, 2, 3, 12, or 24 months).

In another aspect, the invention provides a method of removing the gastrointestinal device of any of the preceding aspects by disengaging the flange from a proximally oriented luminal surface proximal to the pyloric orifice, pulling a drawstring operatively connected to the anchor, and retracting the wave anchor into a retrieval hood or capsule.

BRIEF DESCRIPTION OF THE DRAWINGS

The following drawings are illustrative of particular embodiments of the present invention and are not limiting to various embodiments encompassed by the present invention.

FIG. 4A shows a flange extending radially at about 120° from a distal longitudinal axis. FIG. 4B shows a flange having an extension angle that becomes more acute along its radius. FIG. 4C shows a flange having an extension angle with an acute phase at its central radius and an obtuse phase at a distal radius.

DETAILED DESCRIPTION OF THE INVENTION

Figure 1:
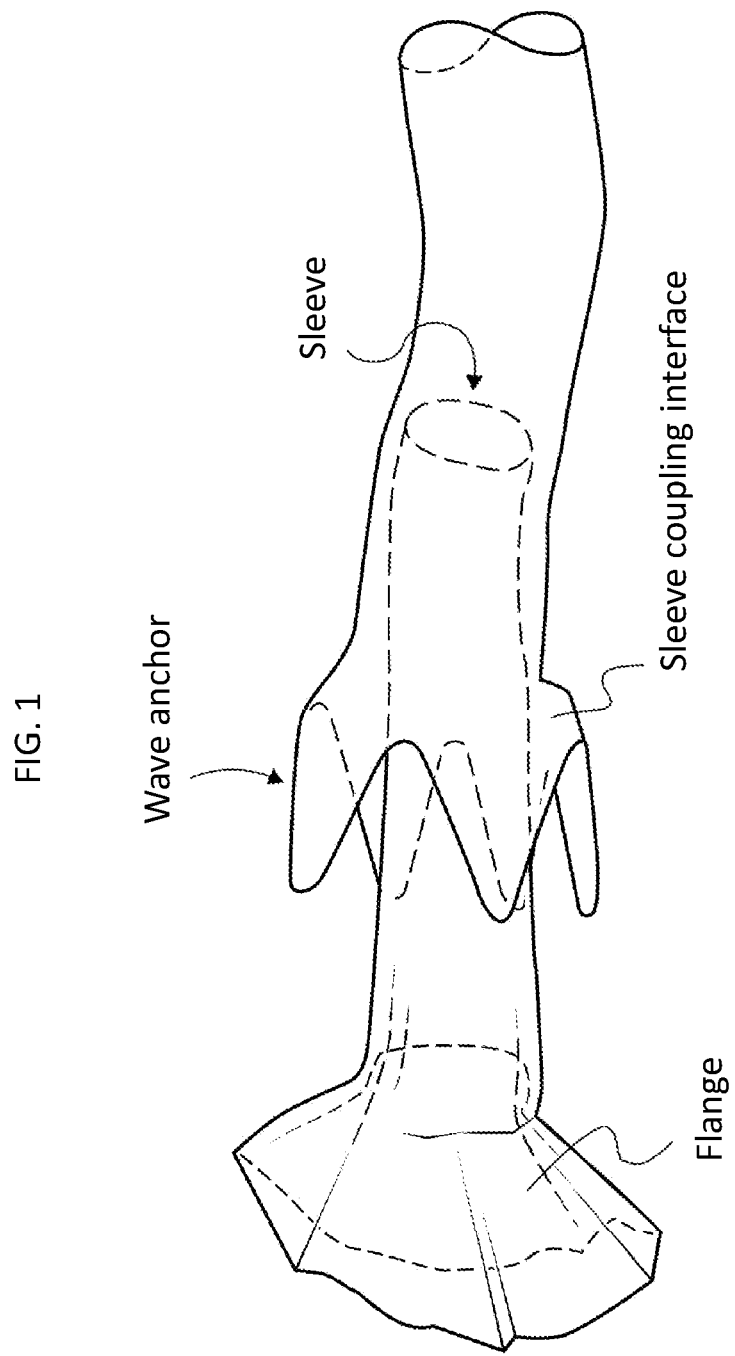
FIG. 1 is a line drawing of a flanged gastrointestinal device having a wave anchor.

The present invention provides gastrointestinal devices for limiting transfer and contact of material across luminal walls along a segment of the gastrointestinal tract (e.g., at the duodenum and/or upper jejunum). Devices of the invention include a liner (e.g., a bariatric sleeve), an anchor for resisting movement of the liner (e.g., proximal and/or distal movement of the liner), and a flange for attachment, e.g., to the pyloric tissue, e.g., by suturing or stapling. Alternatively, devices of the invention include a liner (e.g., a bariatric sleeve), and a flange for attachment, e.g., to the pyloric tissue, e.g., by suturing or stapling. The invention also provides methods of use associated with such gastrointestinal devices. Methods of the invention include methods of implanting gastrointestinal devices in the gastrointestinal tract of a subject, e.g., by deploying an anchor and attaching a flange. Additionally, methods of the invention include methods of implanting gastrointestinal devices in the gastrointestinal tract of a subject, e.g., by attaching a flange. The invention further provides methods for removal of such devices through detaching the flange or by detaching the flange and retrieving the anchor (e.g., by pulling a drawstring to collapse the anchor). Lastly, the invention features methods of treatment, including methods of treating a metabolic disorder, such as type 2 diabetes, non-alcoholic steatohepatitis (NASH), non-alcoholic fatty liver disease (NAFLD), obesity, and related comorbidities thereof by implanting gastrointestinal devices.

Definitions

As used herein, the term "incretin" refers to a compound that directly or indirectly stimulates insulin release, inhibits glucagon release, and reduces gastric emptying. For example, incretins stimulate an increase in the amount of insulin released from the pancreas when plasma glucose levels are elevated relative to normal after food consumption, thereby leading to a decrease in blood glucose levels. Specific examples of incretins include gastric inhibitory peptide (i.e., glucose-dependent insulinotropic polypeptide, or GIP) and glucagon-like peptide-1 (GLP-1), along with their analogs and derivatives.

As used herein, the term "gastrointestinal implant" includes an anchor for securely positioning the device to the stomach and a sleeve to limit absorption of nutrients in the duodenum. A "sleeve," as used herein, refers to a hollow, cylindrical liner that is open at both ends and adapted to extend at least into the duodenum. Partially digested food, or chyme, passing through the GI tract passes through the interior of the sleeve.

As used herein, "flexible" refers to capacity to bend longitudinally, and "collapsible" refers to capacity to bend radially, i.e., to change cross-sectional dimensions and area (e.g., to collapse wholly or partially, e.g., to accommodate peristalsis in the intestine).

As used herein, "sleeve-coupling interface" refers to the point of the sleeve that is connected to anchor by a coupling liner. In some cases, the sleeve-coupling interface circumscribes the sleeve at a point along its length, e.g., at or distal to the distal end of the anchor.

Unless otherwise specified, a longitudinal axis refers to the longitudinal axis of the gastrointestinal tract (i.e., the line running through the gastrointestinal lumen equidistant from the luminal walls). It will be understood that, due to the tortuosity of the gastrointestinal tract, the directionality of its longitudinal axis and associated radial coordinates will vary along its length. For cases in which the "longitudinal axis of the device" is referred to, it is explicitly referred to as such.

The orientation of any surface (e.g., a luminal surface, luminal wall, or device surface) is characterized herein according to the direction of its normal line (i.e., a vector originating at and projecting orthogonally outward from its surface). As used herein, the orientation of a gastrointestinal luminal surface is an average of any micro features and is therefore independent of, e.g., microvilli.

The angle between a normal line and the longitudinal axis of a "proximally oriented" or a "distally-oriented" surface is ≥0° and <90°. For example, a "proximally oriented surface" of a lumen herein refers to a luminal surface that faces in a proximal direction (e.g., the stomach side of the pyloric sphincter), whereas a "distally-oriented surface" of a lumen herein refers to a luminal surface that faces in a distal direction (e.g., the intestinal side of the pyloric sphincter).

The term "pyloric orifice" refers to open area on the plane in which the pyloric opening lies.

The term "pyloric sphincter" refers to the tissue (e.g., epithelial and muscular tissue) that surrounds the pyloric orifice.

As used herein, "radial" refers to any direction that is substantially orthogonal to a reference longitudinal axis (e.g., the longitudinal axis of the anchor). For example, an inward radial force is exerted on a compressed anchor by inner walls of a catheter in which it resides. An outward radial force may be imparted, e.g., by an anchor upon expansion of its radius, e.g., from a radially compressed state to a radially expanded state (e.g., a relaxed or intrinsic state), against a luminal wall.

As used herein, a "flanged" element or a "flange" refers to a projection that, when implanted in a subject, wholly or partially extends radially (i.e., in a direction having a radial component from a longitudinal axis of a pyloric orifice (e.g., between 90° and 180° outward from the longitudinal axis of the pyloric orifice)) and configured to attach a gastrointestinal device to a proximally oriented luminal surface (e.g., a proximal surface of the pyloric sphincter and/or an antral surface of the stomach).

As used herein, an "anchor" refers to an annular element of a gastrointestinal device that resists longitudinal motion (e.g., migration resulting from peristalsis) of the gastrointestinal device by exerting a force against a gastrointestinal luminal wall. An anchor may resist motion of the gastrointestinal device by exerting a radial force on an inward-facing gastrointestinal luminal wall, by exerting a proximal force on a distally-oriented gastrointestinal luminal wall, or by exerting a distal force on a proximally oriented gastrointestinal luminal wall. Anchors may or may not penetrate a gastrointestinal luminal wall (e.g., partial penetration into a gastrointestinal luminal wall or complete penetration through a gastrointestinal wall). A "wave anchor" refers to an anchor having an undulating pattern along its longitudinal axis. Undulations can be sinusoidal or can have another shape or repeating circumferential pattern.

As used herein, to "exert a force" includes (a) transmitting a force, for example, from one region of the gastrointestinal tract to another (e.g., from a distal portion of the duodenal bulb to a distally-oriented surface of the pyloric sphincter) and (b) converting potential energy to force, for example, as occurs during radial expansion of a spring-like anchor against a gastrointestinal luminal wall.

As used herein, "relaxed" and "intrinsic" are used interchangeably to refer to the physical state of an element in an unconstrained environment. A "relaxed diameter" of an anchor refers to its natural or equilibrium diameter prior to loading into a catheter or other device (e.g., a manufacturing device or tool used for catheter loading), in the absence of any external force.

As used herein, to be "directly connected" means that there is no intermediate connecting element.

As used herein, the "compressive elastic deformation diameter" is the limit of diameter compression below which the anchor deforms and will not return to its original relaxed diameter or original relaxed shape. The compressive elastic deformation diameter can be characterized in absolute or relative terms.

As used herein, the term "fluid" refers to digested or partially digested liquid or semisolid material, for example, chyme and digestive secretions.

As used herein, the term "about" refers to ±20% of a recited value.

As used herein, the terms "subject" and "patient" are used interchangeably and refer to any mammal (e.g., a human) having a gastrointestinal tract capable of containing of gastrointestinal implant of the invention. A patient who is being treated for a metabolic disorder, e.g., high blood sugar, diabetes (e.g., type 2 diabetes), obesity, NASH, NAFLD, or a related comorbidity thereof, may be one who has been diagnosed by a medical or veterinary practitioner as the case may be as having such a condition. Diagnosis may be performed by any suitable means. Patients of the invention may have been subjected to standard tests or may have been identified, without examination, as one at high risk of having or developing a metabolic disorder, e.g., type 2 diabetes, pre-diabetes, obesity, NASH, NAFLD, or a related comorbidity due to the presence of one or more risk factors, such as age, genetics, or family history.

As used herein, the term "comorbidity" or "related comorbidity" refers to one or more conditions, syndromes, diseases, or disorders that co-occur with metabolic disorders and can be either directly or indirectly linked to metabolic disorders. For example, metabolic disorder-related conditions may include pre-diabetes, type 2 diabetes, obesity, NAFLD, NASH, dyslipidemia, elevated serum/plasma LDL, elevated VLDL, elevated triglycerides, elevated cholesterol, plaque formation leading to narrowing or blockage of blood vessels, glucose intolerance, myocardial infarction, increased risk of hypertension/stroke, or coronary heart disease. As used herein, "diabetes mellitus type 2" or "type 2 diabetes" (also known as diabetes mellitus type 2, non-insulin-dependent diabetes (NIDDM), obesity-related diabetes, or adult-onset diabetes) refers to a metabolic disorder that is primarily characterized by insulin resistance, relative insulin deficiency, and hyperglycemia.

As used herein, the term "treatment" refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and improved prognosis. In some embodiments, the gastrointestinal implant is used to control metabolic disorders (e.g., type 2 diabetes, NASH, NAFLD, obesity, and related comorbidities). In some embodiments, removal of gastrointestinal implant is provided to delay development of a disease or to slow the progression of a disease.

Gastrointestinal Devices

The present invention features gastrointestinal devices for limiting contact and transfer of material across luminal walls along a segment of the gastrointestinal tract (e.g., at the duodenum and/or upper jejunum). Devices of the invention include a liner (e.g., a bariatric sleeve), an anchor for resisting movement of the liner (e.g., proximal and/or distal movement of the liner), and a flange for attachment to a tissue proximal to the pyloric orifice (e.g., to the pyloric tissue or antrum of the stomach).

Flanges

Gastrointestinal devices of the invention feature a flanged proximal end for attaching the device to tissue of the pyloric sphincter (e.g., a proximal surface of the pyloric sphincter) and/or the antral surface of the stomach. By attaching to a proximally oriented tissue surface, a flange can guide fluid (e.g., chyme) from the stomach into the sleeve while providing resistance to distal migration of the gastrointestinal device, e.g., as a result of peristalsis. In some cases, a flange obviates the need for a barbed anchor. For example, the present invention provides devices that resist distal migration by attachment of a flange at a proximal region (e.g., proximal to the pyloric orifice) and resist proximal migration by physical constraint of an anchor at a distal region (e.g., distal to the pyloric orifice, e.g., within the duodenal bulb). In another example, the present invention provides devices that resist distal migration by attachment of a flange at a proximal region (e.g., proximal to the pyloric orifice) and resist proximal migration that by an eversion resistant sleeve that resists proximal eversion (e.g., aberrant proximal movement through the pyloric orifice that may cause obstruction to the flow of fluid). Eversion resistant sleeves are described in U.S. Pat. No. 7,766,973, which is herein incorporated by reference.

Figure 2:
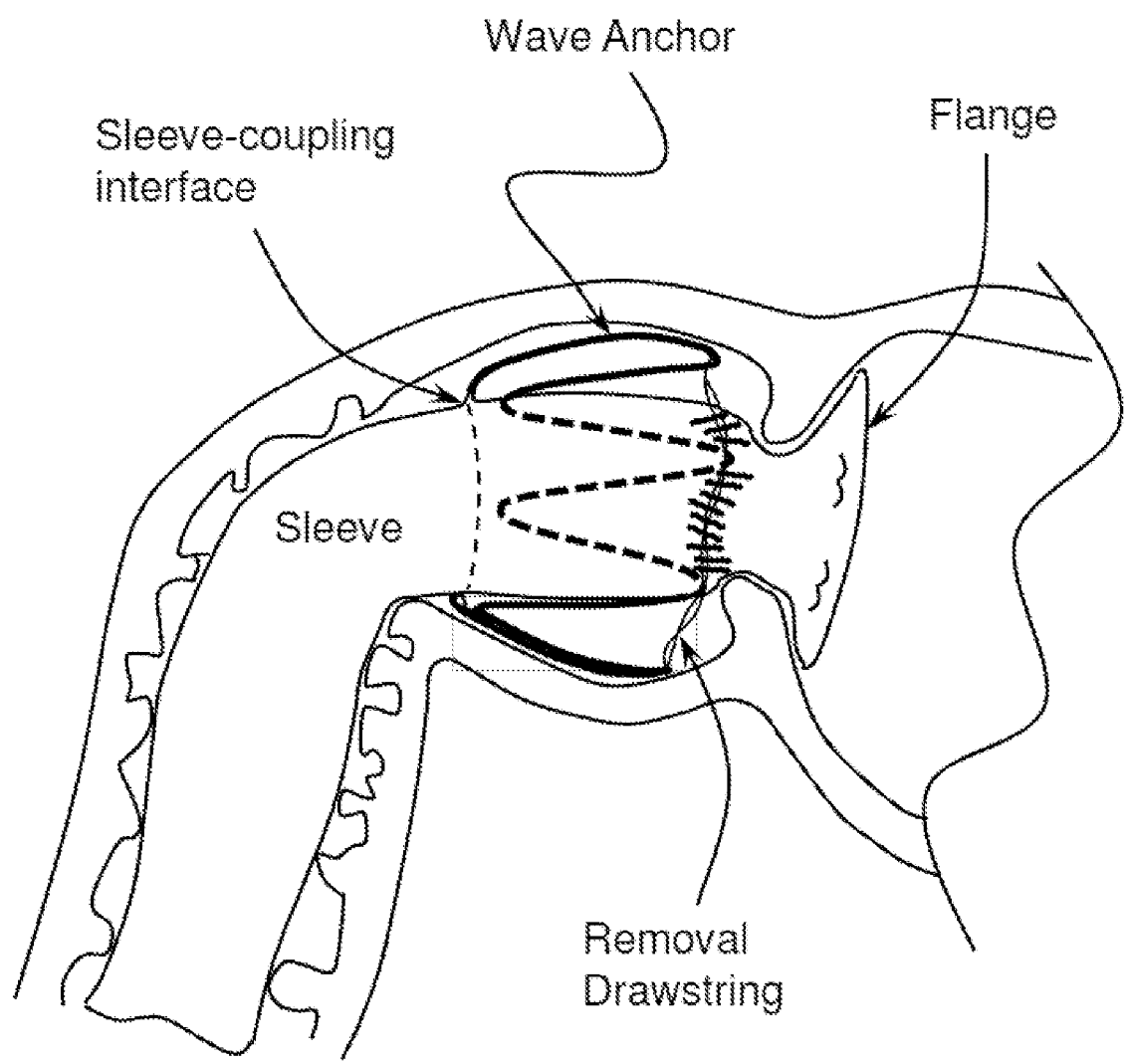
FIG. 2 is a drawing of a flanged gastrointestinal device having a wave anchor in position within a gastrointestinal tract.
Figure 3:
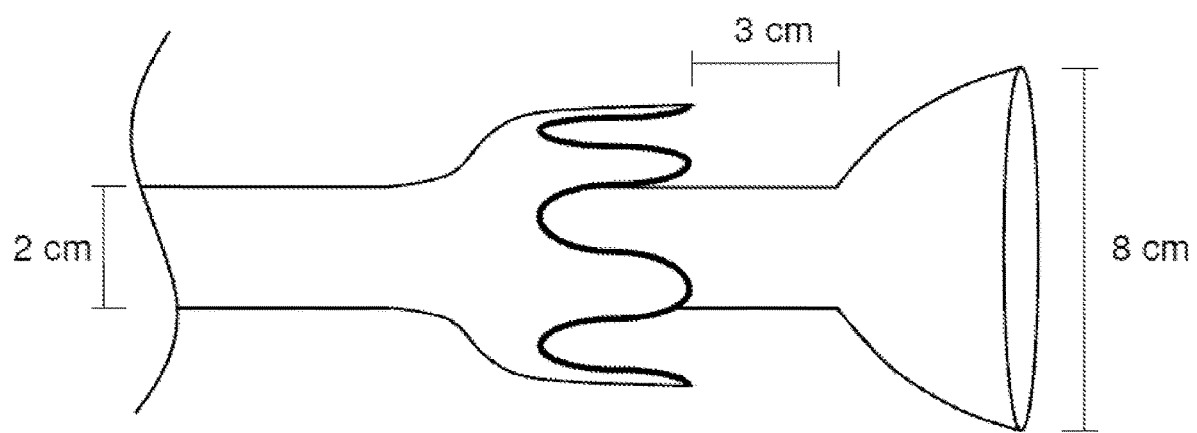
FIG. 3 is a drawing of a flanged gastrointestinal device having a sleeve diameter of 2 cm, a distance of 3 cm from the proximal end of the anchor to the distal end of the flange, and a flange having an outer diameter of 8 cm.

An exemplary flanged gastrointestinal device is shown in FIG. 1, and a cross-sectional drawing of an exemplary flanged gastrointestinal device is shown in FIG. 2. In general, a flange is attached to a proximal portion of the sleeve. In some cases, the flange defines the proximal opening of the sleeve (e.g., as a circular "rim" or "skirt" connected to the proximal end of the sleeve). In some embodiments, the flange extends radially in all directions from the sleeve, which may help prevent fluid from passing around the outside of the proximal end of the sleeve. The outer diameter of the flange may be constant (e.g., substantially circular). In such cases, the outer diameter of the flange can be at least 10% greater than the diameter of all or a portion of the sleeve (e.g., at least 10% greater than, at least 20% greater than, at least 30% greater than, at least 40% greater than, at least 50% greater than, at least 60% greater than, at least 70% greater than, at least 80% greater than, at least 90% greater than, at least 100% greater than, at least 150% greater than, at least 200% greater than, at least 250% greater than, at least 300% greater than, at least 400% greater than, or at least 500% greater than the diameter of all or a portion of the sleeve (e.g., the proximal end of the sleeve)). In some cases, the outer diameter of the flange is about 6-10 cm. In some embodiments, the outer diameter of the flange is about 6 cm, about 7 cm, about 8 cm, about 9 cm, or about 10 cm. In some embodiments, such as in the device shown in FIG. 3, the outer diameter of the flange is 8 cm. The length of the sleeve extending from the distal end of the flange to the proximal end of the anchor ranges from about 1 cm to about 10 cm. In some embodiments, the length of the sleeve extending from the distal end of the flange to the proximal end anchor is about 1 cm, about 2 cm, about 3 cm, about 4 cm, about 5 cm, about 6 cm, about 7 cm, about 8 cm, about 9 cm, or about 10 cm. In some cases, such as in the device in FIG. 3, the length of the sleeve extending from the distal end of the flange to the proximal end of the anchor is 3 cm. In other cases, the length of the sleeve extending from the distal end of the flange to the proximal end of the anchor is 6 cm. The hole in the flange can be suitable to accommodate the diameter of the sleeve (e.g., from 1 to 3 cm, e.g., about 1.1 cm, about 1.2 cm, about 1.3 cm, about 1.4 cm, about 1.5 cm, about 1.6 cm, about 1.7 cm, about 1.8 cm, about 1.9 cm, about 2.0 cm, about 2.1 cm, about 2.2 cm, about 2.3 cm, about 2.4 cm, about 2.5 cm, about 2.6 cm, about 2.7 cm, about 2.8 cm, about 2.9 cm, or about 3.0 cm). The device in FIG. 3 shows a flange having a hole that meets the proximal opening of the sleeve having a diameter of 2 cm.

Alternatively, the flange may extend radially at different lengths around the circumference of the sleeve (e.g., its outer diameter may be variable, e.g., ovoidal or irregularly shaped). Such a configuration may be adapted for an asymmetric anatomy and/or physiological forces (e.g., at the pylorus or antrum of the stomach). Additionally or alternatively, an irregularly shaped outer diameter of a flange may serve to optimize the seal of the flange to the gastrointestinal wall. For example, the outer edge (e.g., outer diameter) of a flange may undulate (e.g., similarly to a sinusoidal wave anchor) to maintain contact to a dynamic luminal wall, e.g., to a bowl-shaped antral wall.

Figure 4A:
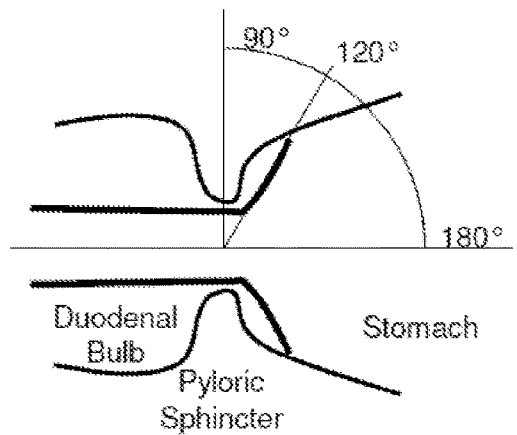
FIGS. 4A-4C are diagrams showing various angles of flange extension.
Figure 4B:
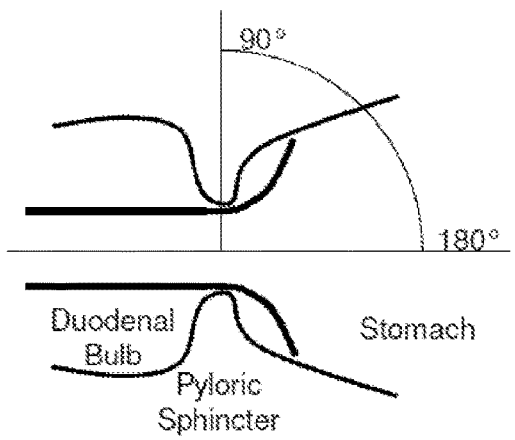
Figure 4C:
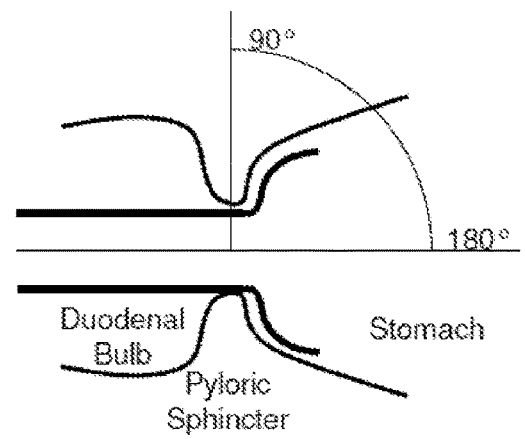

When in position in a subject, a flange extends, wholly or partially, in a direction having a radial component from a longitudinal axis of a pyloric orifice (e.g., between 90° and 180° outward from the longitudinal axis of the pyloric orifice). In some cases, all or most of the flange intrinsically extends radially between 90° and 180°, e.g., at about 100°, about 110°, about 120°, about 130°, about 140°, about 150°, about 160°, or about 170° outward from the longitudinal axis of the pyloric orifice, e.g., the angle of extension is substantially linear along the radius of the flange. In some cases, all or most of the flange intrinsically extends radially at about 120° outward from the longitudinal axis of the pyloric orifice (e.g., the distal longitudinal axis), as shown in FIG. 4A. Alternatively, the flange may extend at angle that varies along its radius. For example, the angle may become more acute as along the radius of the flange, such as shown in FIG. 4B. The angle may also vary in opposing directions over its radius. For example, a flange may become more acute at a central region and gradually become more obtuse (e.g., bowl-shaped) at a greater radius, as shown in FIG. 4C. It will be understood that, once attached to a proximally oriented surface proximal to the pyloric orifice, the angle of extension of the flange will substantially match that of the surface to which it is attached.

Suitable materials for flanges of the present invention include polymeric liners, such as polytetrafluoroethylene (PTFE), expanded PTFE (ePTFE), fluorinated ethylene propylene (FEP), perfluoroalkoxy (PFA), ethylene tetrafluoroethylene (ETFE), and polyvinylidene fluoride (PVDF). The flange can be an extension of the sleeve material (e.g., integrally formed), and it may have a greater thickness than all or a portion of the remainder of the sleeve. The thickness of the flange will depend on means of attachment to a subject.

A flange can be attached to a sleeve by any suitable means known in the art. In some cases, the proximal end of the sleeve is cut longitudinally at one or more points along its circumference, creating strips of sleeve material, which can be splayed out and attached to a flange. In some embodiments, these portions of the sleeve can be sandwiched between two flange pieces. The two flange pieces (e.g., donut-shaped portions of PTFE/FEP) can then be attached to one another, for example, by hand soldering, to entrap the sleeve portions therebetween such that the sleeve lumen passes through the holes in the flange. Other methods of attaching the flange to the sleeve are known in the art.

Anchors

Gastrointestinal devices of the invention are configured to be retained within the gastrointestinal tract (e.g., within the duodenum, e.g., within the duodenal bulb) using one or more annular anchors, which resist longitudinal motion of the device through the gastrointestinal luminal wall. In some embodiments, an anchor works in tandem with a flange to resist longitudinal migration, i.e., the anchor resists proximal migration while the flange resists distal migration. In some cases, the anchor and the flange work in concert (or, alternatively, independently) to resist radial motion.

The anchor can be attached to sleeve by any means suitable to longitudinally tether the sleeve to the anchor (e.g., to prevent longitudinal motion of the sleeve relative to the anchor). In some cases, the anchor is connected to the sleeve by a coupling liner. The coupling liner may be the same or a similar material to that of the sleeve and projects from the sleeve at a sleeve-coupling interface, which forms the point of connection between the anchor and the sleeve. In cases in which the sleeve runs longitudinally through the center of the anchor, the coupling liner may connect to the sleeve around the full circumference of the sleeve. For example, the coupling liner may connect the anchor to the sleeve at a point on the sleeve that is at or distal to (e.g., less than 1 inch distal to) the distal end of the anchor. Such a configuration, in which the sleeve-coupling interface is beyond the overlapping anchor, may allow for radial displacement (e.g., partial collapse) of the anchor without substantially collapsing the sleeve (e.g., at or proximal to the sleeve-coupling interface).

An anchor of the present device can be distal to the flange and proximal to all or a majority of the sleeve. In some cases, the sleeve runs longitudinally through the anchor (e.g., such that the anchor is coupled to the sleeve at a point that divides the sleeve into a proximal portion and a distal portion). Thus, the relaxed diameter of the anchor may exceed a maximum diameter of all or a portion of the sleeve (e.g., by between 10% and 200%, e.g., by 10%, 20%, 30%, 40%, 50%, 60%, 70%, 80%, 90%, 100%, 110%, 120%, 130%, 140%, 150%, 160%, 170%, 180%, 190%, 200%, or more). In some cases, the anchor may exert an outward radial force on all or a portion of the sleeve (e.g., to maintain the sleeve in an open or partly open position) and/or the gastrointestinal wall (e.g., at the duodenal bulb).

A suitable anchor of the present gastrointestinal device can be a wave anchor, characterized by an undulating pattern along its longitudinal axis. Wave anchors are known in the art and described, for example, in U.S. Pat. Nos. 7,608,144, 8,137,301, 8,162,871, 9,155,609, 7,695,446, 7,678,068, 7,476,256, 7,682,330, 7,981,163, 8,834,405, 9,237,944, 7,815,589, 8,303,669, 8,628,583, 9,084,699, 7,976,488, and 8,425,451, each of which is incorporated herein by reference. In embodiments featuring a wave anchor, the coupling liner can be connected to the sleeve analogously to the connection of the wave anchor to the sleeve in any of the aforementioned references. For example, the coupling liner may be cut back to match the undulating shape of the wave anchor, such that the proximal edge of the coupling liner matches the shape of the wave anchor (e.g., forming a "tulip" shape). Such a configuration can facilitate the formation of a seal at the wave anchor, because proximal ends of the different "petals of the tulip" can flex independently as the coupling material does not restrain them. Additionally, the tulip-shaped proximal end, when installed, forms a secure seal along its entire perimeter when implanted in the gastrointestinal tract. Advantageously, such a tailored fit leaves no unsupported material between the edges of the device that ingested material can get behind.

Suitable anchors can be manufactured from a resilient metal such as a heat-treated spring steel, stainless steel, or from an alloy such as nitinol (NiTi). Anchors, such as wave anchors, can be made from nitinol wire (e.g., from 0.01" to 0.03" nitinol wire). For example, Anchors up to 60 mm diameter have been fabricated from 0.023" Nitinol wire (see, e.g., U.S. Pat. No. 8,425,451). The wire diameter of the anchor can be adjusted to provide the desired force. Typically, shorter anchors use thinner wires. For example, a 19 mm long anchor was made from 0.016" diameter wire to provide the same compliance as the 32 mm long anchors shown (Id.). As the diameter of the wire becomes larger, the compressive elastic deformation diameter increases.

Other alloys include nickel-cobalt-chromium-molybdenum alloys possessing a unique combination of ultrahigh tensile strength, such as MP35N. Additionally, the anchor can be formed from a polymer and/or a composite having similar properties. The anchor can be manufactured from a single strand, such as a wire, contoured into the desired shape. Alternatively, the disclosed anchor can be manufactured from multi-strands of the same or different materials similarly contoured to the desired shape. In some embodiments, a wave anchor can be cut into the wave shape from tubular stock of the desired material, such as nitinol.

In some cases, the anchor includes attaching means adapted to secure the anchor to the gastrointestinal tract (e.g., the duodenum, e.g., the duodenal bulb). The attaching means can include an interference fit, chemical fasteners, mechanical fasteners, or the like. For example, the anchor can be attached to the surrounding anatomy using an interference fit provided by the relative size of the anchor in relation to the surrounding anatomy. Alternatively or in addition, the anchor can be attached to the surrounding anatomy using chemical fasteners, such as surgical adhesives. Mechanical fasteners can include, for example, sutures, surgical staples, barbs, or the like. In some embodiments, the mechanical fasteners can be dissolvable, dissolving after a predetermined time and allowing the device to pass naturally. Mechanical fasteners can include barbs that extend from the exterior surface of the anchor for anchoring the proximal portion of the sleeve to the muscular tissue of the surrounding anatomy. The barbs may be bi-directional for anchoring the proximal portion of the flexible sleeve to the intestine. Barbs may be bi-directional and aligned with the peristaltic axis of the gastrointestinal tract, i.e., some barbs are pointed in the direction of forward peristalsis to secure the anchor against forward motion through the gastrointestinal tract, and some barbs are pointed opposite the direction of forward peristalsis, to secure the anchor against reverse motion in the gastrointestinal tract. Typically, the barbs secure the anchor to muscular tissue of the intestine. In various embodiments, the barbs extend from the surface exterior surface of the anchor by about 2 mm or greater.

In other cases, the anchor is configured to provide adequate longitudinal support without the need for barbs (e.g., by sharing some of the forces with the flange of the present device). Accordingly, these gastrointestinal devices feature anchors that are not configured to puncture a gastrointestinal lumen.

The effects of varying the mechanical properties of various anchor designs have been studied and reported, for example, in U.S. Pat. No. 8,425,451, which is incorporated herein by reference. In general, it is believed that the stiffness or compliance of the anchor can determine the ability of the device seal against the tissue and to maintain any attaching means, e.g., barbs engaged in the tissue. The anchor should be sufficiently elastic to permit loading and delivery in a small capsule (e.g., max outer diameter of 16 mm, practical inner diameter of 12 mm) for implantation, followed by full expansion into the intestine. The diameter of the device should also be able to accommodate the full natural dilation of the tissue. Thus, the relaxed diameter of the anchor may be greater than 30 mm (e.g., greater than 35 mm, greater than 40 mm, greater than 45 mm, greater than 50 mm, greater than 55 mm, or greater than 60 mm). If the compliance of the anchor is too high (too soft), the anchor may separate from the tissue and cause leaks and/or migrations. If the anchor compliance is too low (too stiff), it may cause irritation to the tissue and/or require a larger capsule for delivery to avoid compressing beyond its elastic deformation diameter. Generally, the more nodes included in the undulating wave pattern, the more compliant the device will be. Additionally, the larger the filament or wire diameter, the less compliant the device will be. In some embodiments, such as laser-cut devices, both the width and thickness of the wire (e.g., rectangular profile) can be varied. Thus, the overall compliance of the device is determined at least from the wave pattern and the wire shape and/or diameter. In some embodiments, the wave anchor has at least four nodes (e.g., five, six, seven, eight, nine, or more nodes).

In various embodiments, the anchor is characterized by a radial force of about 0.1 Newtons (N) or greater at a compressed diameter of 25 mm. In some cases, the radial force at 25 mm compression is about 0.3 N or greater, e.g., about 0.4 N or greater, or between about 0.5 N and about 1.5 N. Additionally or alternatively, the anchor may characterized by an average spring rate of about 13 N per meter (N/m) or greater in a range of motion, the range of motion being within a diameter range defined by a relaxed diameter and a compressive elastic deformation diameter. More particularly, the average value of the spring rate may be between about 15 N/m and about 35 N/m. In some embodiments, the spring rate is substantially constant over the range of motion, i.e., the force versus displacement data is substantially linear over the range of motion.

Additionally or alternatively, the anchor may be characterized by a radial force over the range of motion of about 0.1 N or greater, e.g., about 0.2 N or greater, about 0.3 N or greater, or about 0.4 N or greater.

In some embodiments, the range of motion is about 20 mm or greater, e.g., about 30 mm or greater, or about 35 mm or greater. The range of motion can be a percentage of the relaxed diameter of the anchor of about 30% or greater.

The anchor may also be characterized by a relaxed diameter. Generally, the relaxed diameter can be about 40 mm or greater, e.g., about 45 mm or greater, or between about 45 mm and about 65 mm. In particular embodiments, the relaxed diameter is about 50 mm or about 60 mm.

An anchor can have a radial force being about 0.4 N or less at a diameter of 55 mm, e.g., at a diameter of 50 mm, 45 mm, or 40 mm. In various embodiments, the anchor can be characterized by the radial force being about 0.3 N or less at a diameter of 55 mm or less, e.g., at a diameter of 50 mm, 45 mm, or 40 mm. In various embodiments, the anchor can be characterized by the radial force being about 0.2 N or less at a diameter of 55 mm or less, e.g., at a diameter of 50 mm, 45 mm, or 40 mm.

The anchor can be characterized by a compressive elastic deformation diameter which can be expressed in absolute or relative terms. In various embodiments, the compressive elastic deformation diameter is about 12 mm or less, e.g., about 8 mm or less. In some cases, the compressive elastic deformation diameter is a percentage of the relaxed diameter of about 30% or less, e.g., about 20% or less.

At least one advantage resulting from anchoring at the duodenal bulb is that the pyloric orifice may be allowed to open and close normally. As described above, the length of the anchor is minimal to ensure that the ampulla of vater is not blocked. The distance in an average adult human between the pylorus and the ampulla of vater is at least about 2 inches. Thus, the length of the anchor is preferably less than about 2 inches (e.g., between 0.5 and 2 inches, e.g., about 0.5 inches, about 0.6 inches, about 0.7 inches, about 0.8 inches, about 0.9 inches, about 1 inch, about 1.1 inches, about 1.2 inches, about 1.3 inches, about 1.4 inches, about 1.5 inches, about 1.6 inches, about 1.7 inches, about 1.8 inches, about 1.9 inches, or about 2 inches).

Anchors can be configured with a drawstring for removal of the device according to methods described below. In particular, a drawstring connecting multiple proximal elements of the anchor (e.g., each proximal node of a wave anchor) can function to radially compress the proximal portion of the anchor upon being pulled in a proximal direction, e.g., by a hook-tipped catheter. Drawstring configurations are known in the art and described, for example, in U.S. Pat. Nos. 7,608,114, 8,137,301, 8,162,871, 9,155,609, 7,476,256, 7,682,330, 7,981,163, 8,834,405, 9,237,944, 8,057,420, 8,771,219, and 9,095,416, each of which is incorporated herein by reference.

Sleeves

Gastrointestinal sleeves suitable for adaptation for the presently disclosed gastrointestinal devices are known in the art and described, e.g., in U.S. Pat. Nos. 7,025,791, 7,608,114, 7,695,446, 7,678,068, 7,122,058, 7,476,256, 7,815,589, 7,837,643, 8,057,420, 7,815,591, 7,771,382, and 7,766,973, each of which is incorporated herein by reference.

Figure 5:
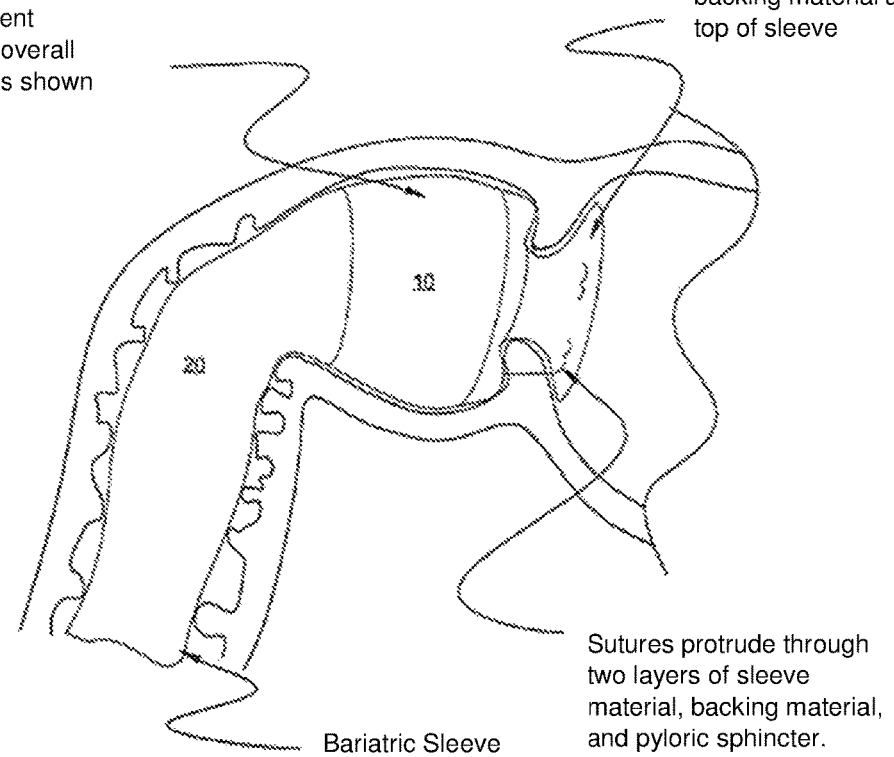
FIG. 5 is a drawing of another embodiment of a flanged gastrointestinal device having a stent-like anchor.
Figure 6:
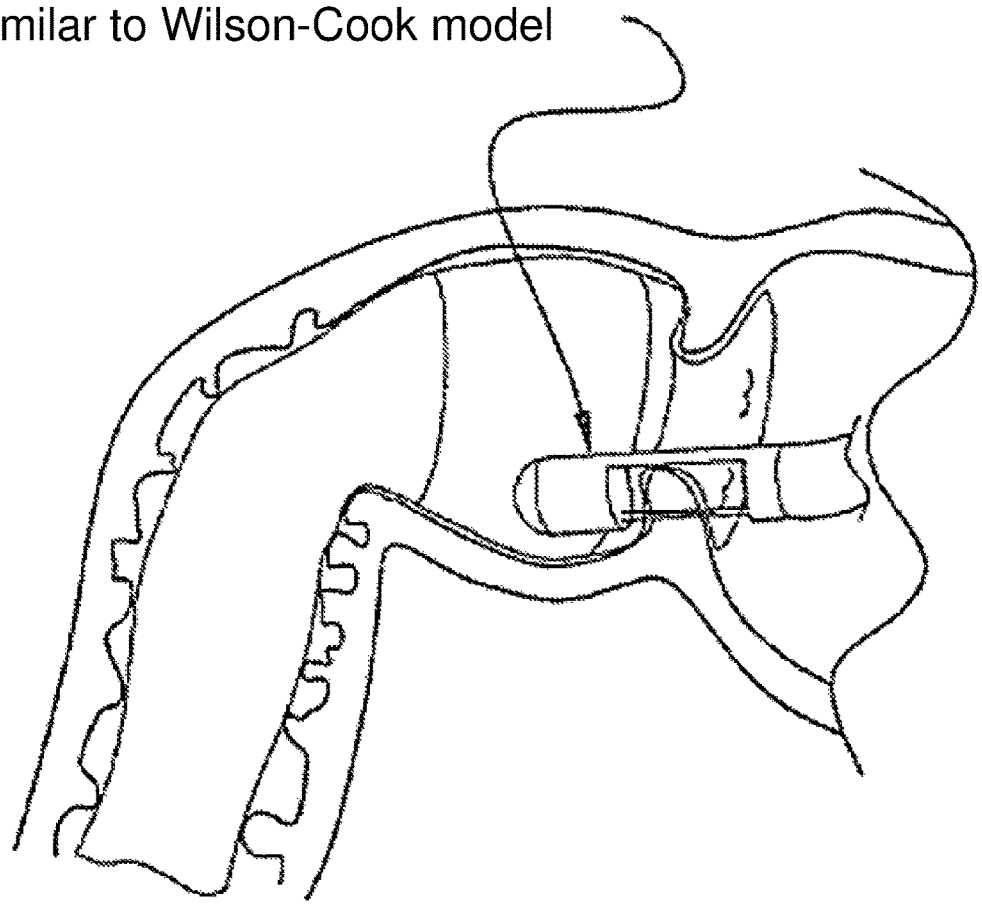
FIG. 6 is a drawing of a flanged gastrointestinal device being implanted in a gastrointestinal tract by endoscopic suturing.
Figure 7:
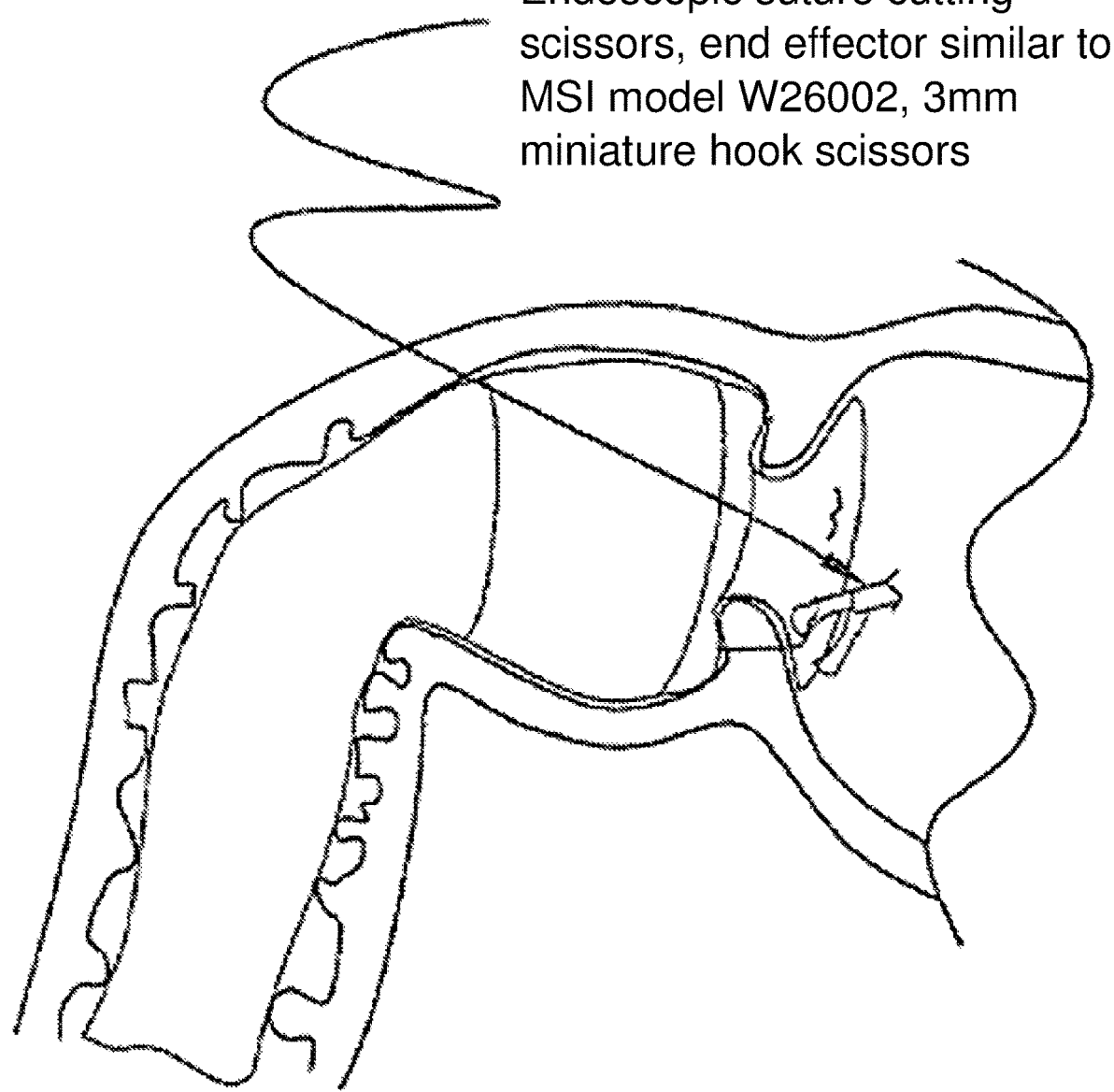
FIG. 7 is a drawing of a flanged gastrointestinal device of the invention being removed from a gastrointestinal tract by endoscopic suture cutting.

Sleeves of the present device may be connected to an anchor for positioning distal to the pyloric orifice (e.g., at the duodenal bulb) and to a flange for attachment to a luminal wall proximal to the pyloric orifice (e.g., at a proximally oriented surface of the pyloric sphincter or the antrum of the stomach). As such, a sleeve is configured to receive fluid from the stomach as it moves past the flange, through the pylorus. The anchor is connected (e.g., at a sleeve-coupling interface) to the sleeve at a position distal to the flange or proximal end of the sleeve (e.g., from 1-6 inches distal to the flange or proximal end of the sleeve, e.g., about 1 inches, about 2 inches, about 3 inches, about 4 inches, about 5 inches, or about 6 inches distal to the flange or proximal end of the sleeve). In some cases, a sleeve-coupling interface divides the sleeve into a proximal portion and a distal portion). The proximal portion and distal portion may be substantially similar in material, wall-thickness, intrinsic diameter, and other physical properties. In other embodiments, the intrinsic diameter of the sleeve varies along its length, such as shown in FIGS. 5-7.

In general, sleeves of the gastrointestinal device are thin-walled, collapsible, flexible, and floppy (i.e., they do not support the entirety of their weight, for example, if stood on end, they would buckle). Thus, sleeves can reduce or eliminate contact of fluid with walls of the intestine or digestive solutions secreted therefrom while transmitting natural peristaltic forces to propel the fluid through the intestines. After fluid from the stomach has passed through the sleeve, the sleeve may become thin and floppy, permitting the sleeve to contour to the inner walls of the intestine. In some cases, the sleeve is substantially non-compliant and drapes away from the intestinal walls, thereby permitting pancreatic juices to flow unimpeded into the duodenum through the ampulla of vater. Passage of fluid through the sleeve is also enhanced if the sleeve is made from a material having a low coefficient of friction (e.g., a static or kinetic coefficient of friction of less than about 0.3, e.g., about 0.29, about 0.28, about 0.27, about 0.26, about 0.25, about 0.24, about 0.23, about 0.22, about 0.21, about 0.2, about 0.19, about 0.18, about 0.17, about 0.16, about 0.15, about 0.14, about 0.13, about 0.12, about 0.11, about 0.1, or less).

Such properties can be found in a sleeve formed from a fluoropolymer, such as expanded polytetrafluoroethylene (ePTFE), or from a combination with another material. For example, one such combination includes an ePTFE layer of material combined with a different fluoropolymer layer, such as fluorinated ethylene-propylene (FEP). The combination of the FEP with ePTFE provides a low coefficient of friction while also being substantially non-permeable. In some embodiments, another material such as PTFE is applied to an ePTFE substrate using vapor deposition. Alternatively or in addition, the sleeve can be formed using polyolefin films, such as low density polyethylene (LDPE), high density polyethylene (HDPE), and polypropylene. Other materials suitable for use as part of a sleeve include cast polytetrafluoroethylene (e.g., TEFLON™), cast PTFE with FEP or perfluoroalkoxy (PFA) coating on a PTFE to minimize pin holes, extruded FEP and extruded PFA. These materials are solid and substantially non-porous in contrast to ePTFE, which is generally porous. These materials are also considered to be fluoropolymers. In some cases, the wall thickness of the sleeve is less than about 0.0025 inches (e.g., between 0.0003 and 0.0025 inches, e.g., from 0.0003 to 0.0010 inches, from 0.0010 to 0.0015 inches, from 0.0015 to 0.0020 inches, or from 0.0020 to 0.0025 inches, e.g., about 0.001 inches).

The length of the sleeve ranges from about one foot to about five feet (e.g., about 30 cm to about 150 cm). In some cases, the length of the sleeve is from 1 to 3 feet (e.g., 30 cm to 90 cm) from its proximal end (e.g., at flange) to its distal end (e.g., below the ligament of Treitz). In some embodiments, the sleeve has a length of 12 inches, 13 inches, 14 inches, 15 inches, 16 inches, 17 inches, 18 inches, 19 inches, 20 inches, 21 inches, 22 inches, 23 inches, 24 inches, 25 inches, 26 inches, 27 inches, 28 inches, 29 inches, 30 inches, 31 inches, 32 inches, 33 inches, 34 inches, 35 inches, or 36 inches, e.g., about 30 cm, about 35 cm, about 40 cm, about 45 cm, about 50 cm, about 55 cm, about 60 cm, about 65 cm, about 70 cm, about 75 cm, about 80 cm, about 85 cm, about 90 cm, about 95 cm, about 100 cm, about 110 cm, about 120 cm, about 130 cm, about 140 cm, or about 150 cm. The length of the sleeve can be selected to bypass the duodenum and a portion of the jejunum. The length may be increased to further decrease absorption by bypassing a longer section of the jejunum. Thus, the length of the sleeve is variable and may dependent on the patients height, weight, or body mass index.

The sleeve can have a diameter similar to that of a normal subject's intestine, e.g., at the duodenum or jejunum. Additionally or alternatively, the diameter (e.g., maximum diameter) of the sleeve can be from 0.5 to 3 inches (e.g., from 1.0 to 2.0 inches, e.g., about 1.5 inches). By maximum diameter is meant the diameter when the sleeve is open and has a substantially circular cross-section.

In some cases, the invention provides eversion resistant sleeves. Eversion resistant sleeves refer to sleeves that resist proximal eversion (e.g., aberrant proximal movement through the anchor and/or pyloric orifice that may cause obstruction to the flow of fluid). Eversion resistant sleeves may be made from a thickening of the sleeve material, e.g., at a portion of the sleeve distal to the anchor, for example, as described in U.S. Pat. No. 7,766,973, which is herein incorporated by reference.

In some embodiments, markings can be added to the sleeve (e.g., at its exterior surface) to detect the position and orientation of the sleeve on a fluoroscopic image and whether the sleeve is twisted. For example, a stripe can be painted down the length of the device using tantalum impregnated ink, or tantalum bands can be bonded to the exterior surface of the device.

Coupling Liners

The present invention provides a gastrointestinal device featuring a coupling liner that connects to the sleeve at a sleeve-coupling interface. The coupling liner can be fastened to the sleeve by mechanical and/or chemical bonding, soldering, welding, and/or using other mechanical attachment means know in the art. The sleeve can be within the anchor. The sleeve can be fastened to the anchor by mechanical and/or chemical bonding, soldering, welding, and/or using other mechanical attachment means know in the art. In other embodiments, the present invention provides a gastrointestinal device featuring a coupling liner that connects the anchor to the sleeve at a sleeve-coupling interface. The coupling liner can be fastened to the anchor by mechanical and/or chemical bonding, soldering, welding, and/or using other mechanical attachment means know in the art. In some embodiments, the coupling liner includes two layers of material. A first outer layer covers the exterior of the anchor, and a second inner layer covers the interior surface of the anchor. As described above, a drawstring may be threaded through the anchor and/or the coupling liner.

Alternatively, the coupling liner may be integrally formed with the sleeve. In some cases, the coupling liner is attached to the sleeve completely to form a seal around the circumference of the sleeve, e.g., to prevent passage of material longitudinally around the outside of the sleeve. In some embodiments, the coupling liner prevents retrograde passage of fluid.

In some embodiments, the coupling liner is wholly or partially made of the same material as the sleeve. The coupling liner can be wholly or partially made of PTFE, ePTFE, FEP, PFA, ETFE, or PVDF.

Methods

The invention further provides methods for delivering and retrieving flanged gastrointestinal devices, as well as methods of treating metabolic disorders, such as type 2 diabetes, non-alcoholic steatohepatitis (NASH), non-alcoholic fatty liver disease (NAFLD), obesity, and related comorbidities thereof.

Methods of Delivery

Featured herein are methods of delivering the gastrointestinal implant of any embodiment described above. In particular, the methods include attaching the flange to a proximally oriented luminal surface proximal to the pyloric orifice of a subject (e.g., a human patient), such as a proximal surface of the pyloric sphincter or antral surface of the stomach. The region to which the flange is attached will depend on subject anatomy and/or flange design (e.g., the outer diameter of the flange and/or the shape of the flange). Methods of attaching the flange proximal to the pylorus can be adapted for use with currently known methods of delivering anchored gastrointestinal devices for placement distal to the pylorus. Such methods are described, for example, in U.S. Pat. No. 7,837,643, which is incorporated herein by reference.

In some cases, the device is anchored in the duodenal bulb. For purposes of anchoring a gastrointestinal device, the duodenal bulb offers several advantages over other areas in of gastrointestinal tract. First, the duodenal bulb is proportionally sized to capture an anchor. That is, it provides a cavity having a relatively large diameter bounded by anatomies having smaller diameters in both the proximal and distal directions. Thus, the duodenal bulb is naturally configured to retain a suitably shaped anchor. Additionally, the duodenal bulb is relatively less active than either the pylorus or the distal portions of the duodenum. Movement of the surrounding tissue can act to dislodge an anchor over time. The duodenal bulb, at least in part, acts as a holding area for fluid received from the stomach. Thus, the duodenal bulb provides a more stable anchoring platform as there is relatively less movement than at other portions of the gastrointestinal tract.

A proximal portion of the small intestine (e.g., the duodenum) can be expanded in order to create a working space for the practitioner. One method of expanding a proximal portion of the small intestine is to direct a fluid into the duodenum via a working channel in the endoscope. Examples of suitable fluids include gases (e.g., air, nitrogen, and/or carbon dioxide) or liquids (e.g., water and/or saline). In some embodiments, the fluid is a liquid mixture of saline and a contrast medium. Examples of suitable contrast mediums include a fluorescent material, a radiopaque material, or a contrast medium commonly used for intravenous urography (e.g., preparations of diatrizoate sodium and diatrizoate meglumine). The liquid can be a mixture of about 75% saline and about 25% RENOGRAFIN™ (available from Bracco Diagnostics, Inc. Corporation, East Princeton, N.J.).

The exact amount of fluid needed to sufficiently expand the duodenum will depend on variables such as the size of the patient's gastrointestinal tract, the preferences of the practitioner, and/or the length of the gastrointestinal device to be delivered. In some embodiments, at least 60 milliliters of a fluid are used to expand the duodenum. In further embodiments, at least 200 milliliters of a fluid are used to expand the duodenum. 200 milliliters of a fluid would be useful for delivering, for example, a gastrointestinal sleeve that is about two feet in length. In further embodiments, at least 500 milliliters of a fluid are used to expand the duodenum. In still further embodiments, about 600 milliliters of a fluid are used to expand the duodenum which would be useful for delivering, for example, a gastrointestinal sleeve that is about 4 feet in length.

After the small intestine has been expanded to the desired extent, a length of guidewire is directed through the working channel of an endoscope and into the proximal portion of the duodenum. An example of a suitable guidewire is about a 13-foot length of super-stiff 0.035 inch guidewire. Once a sufficient length of guidewire is in the desired location, the endoscope may be removed.

Once the guidewire is in the desired location, the endoscope may be removed, or may remain or be re-introduced at any point for delivery assistance. A delivery catheter can be directed into the duodenum. The leading or distal end of the catheter can be attached, assembled to, or include a capsule or container defining a guidewire lumen along its side. The proximal end of the guidewire can be directed through the guidewire lumen, and the catheter can be advanced or directed along the guidewire to a point distal from the pylorus and into a desired position in the gastrointestinal tract (e.g., a position distal to the pylorus in the duodenal bulb). Once the container is at the desired location in the duodenum, the guidewire can be removed from the gastrointestinal tract.

The container can house all or a portion of a gastrointestinal device, e.g., any gastrointestinal device described above. After the container is at the desired location in the proximal duodenum, a distal portion of the sleeve is removed from the container and directed into a location in the gastrointestinal tract that is distal from the container. The distal portion of the sleeve can be moved independently from the rest of the gastrointestinal device by moving an inner catheter (e.g., tethered to the distal portion of the sleeve) relative to an outer catheter (e.g., tethered to the anchor, flange, and/or proximal portion of the sleeve). Using an atraumatic tip to lead the distal portion of the sleeve, the sleeve can be extended into the distal part of the duodenum or a portion of the jejunum.

After the distal portion of the sleeve is advanced to a desired location in the distal intestine, the anchor can be deployed from the container and anchored to the duodenal bulb. During or after release of the anchor, the flange can be deployed. The flange can be positioned proximal to the pylorus using forceps (e.g., with visual assistance of an endoscope). The flange is introduced across the pylorus and antrum and further secured to the antral wall with an attachment element, such as a suture or a staple.

The flange can be attached to a proximally oriented luminal surface (e.g., a pyloric sphincter or the antral surface of the stomach) by transmission of a distal force from an attachment element to the proximally oriented luminal surface. For example, the distal force can be directed (e.g., endoscopically) to an attachment element, such as a suture or a staple, to secure the flange to the luminal wall (e.g., by sequentially puncturing the flange and luminal wall, or by threading an eyelet or similar opening in the flange to access the luminal wall). One embodiment of a method of attaching the flange to a proximal surface of the pyloric sphincter is illustrated by FIG. 6, showing suturing by an endoscopic suturing device similar to Wilson-Cook model ESD-5. Additionally or alternatively, any suitable method of securing a film, liner, or membrane to a tissue can be used.

Methods of Removal

The invention further provides methods of removing the gastrointestinal device from a subject (e.g., a human patient). In general, the gastrointestinal device can be removed endoscopically by disengaging the flange from the proximally oriented luminal surface proximal to the pyloric orifice and retracting the anchor by pulling a removal drawstring. Thus, in some embodiments, the methods of removal include removing one or more staples from a proximally oriented surface proximal to the pyloric orifice. Additionally or alternatively, the method of removal can involve suture removal, such as shown in FIG. 7.

After removal of the flange, known methods of retrieving an anchored gastrointestinal device (e.g., devices including an anchor and a gastrointestinal sleeve) can be adapted as part of the presently disclosed methods of removal. Such methods are described, for example, in U.S. Pat. Nos. 8,057,420, 8,771,219, and 9,095,416, each of which is incorporated herein by reference.

In some embodiments, the methods of removal include engaging a feature on the gastrointestinal device (e.g., a removal drawstring on the anchor). For example, a grasper, such as a hook, can be included as part of a catheter and delivered to the site of the anchor and engage a removal drawstring that can, e.g., reduce at least one dimension (e.g., diameter, e.g., proximal diameter) of the anchor upon being pulled proximally. In some embodiments, the reduced proximal diameter of the anchor enables an operator to pull the anchor (e.g., an anchor attached to all or a portion of the remainder of the device) into an outer tube for retrieval proximally.

In some embodiments, the outer tube may include a retrieval hood, e.g., attached at its proximal end. The retrieval hood may generally be conical in shape. In some cases, the retrieval hood has openings at both a proximal end and a distal end. The distal end of the retrieval hood may be flared to facilitate capture of an implantable device to be repositioned. In some embodiments, the retrieval hood is made of a flexible material to facilitate its atraumatic placement within a body and to better accommodate at least the proximal portion of the implantable device prior to repositioning. The retrieval hood may be made of a transparent, biocompatible rigid plastic such as polycarbonate or a flexible polymer such as polyurethane, PVC or silicone. Once captured in the retrieval hood, the gastrointestinal device can be safely removed from the body.

Methods of Treatment

Further provided herein are methods of treatment using a gastrointestinal implant of the invention. In particular, the invention provides a method of treating a metabolic disorder by implanting a gastrointestinal device by attaching the flange to a proximally oriented luminal surface proximal to the pyloric orifice (e.g., a proximal surface of the pyloric sphincter or the antrum of the stomach). Metabolic disorders treatable by such methods include type 2 diabetes, NASH, NAFLD, obesity, and related comorbidities thereof. Any of the gastrointestinal devices described above, delivered by any suitable method described above, can be used to treat a metabolic disorder.

Gastrointestinal devices of the invention have been shown to provide negative feedback within the enteric and/or nervous systems, reduced fat digestion, and reduced desire for food. Reduced fat digestion occurs because the sleeve delays the mixing of bile and pancreatic juices with chyme from the stomach until after the chyme leaves the sleeve. Reduced desire for food may occur because the sleeve reduces hormonal release from the duodenum. Additionally, providing poorly digested food to distal portions of the intestine, such as to the ileum, can trigger hormones that reduce appetite. Thus, such gastrointestinal devices can be used for treatment of various metabolic disorders (e.g., type 2 diabetes, NASH, NAFLD, and obesity) characterized by aberrant physiological response to ingested food, such as the incretin effect.

Placement of the gastrointestinal implant device may result in ingested food not digesting in a normal manner and modification of normal triggering of gut hormones. These hormones result in several physiology changes that impact hunger and digestion. Gut hormones that can be modified by devices of the invention include peptide YY (PYY), cholecystokinin (CCK) and ghrelin.

As under-digested food enters the ileum or distal part of the small intestine, PYY is released. PYY has been shown to have a direct effect on appetite, reducing it when released. Undigested food in the ileum indicates that too much food has been ingested. Thus, dependent on the length of the sleeve, the gastrointestinal device can promote deposition of undigested or partially digested food to the distal bowel. Therefore, the placement of a sleeve in the intestine promotes the delivery of undigested food to the ileum, which in turn promotes the release of PYY and reduces appetite in humans.

The hormone CCK is released when food contacts the duodenum. CCK triggers the release of bile from the gallbladder. Therefore, placing a sleeve in the duodenum reduces the release of CCK and thus reduces bile output resulting in reduction in the digestion of food.

Some ghrelin is released when food contacts the duodenum. Ghrelin has been shown to be a factor in the control of appetite. Gastrointestinal devices of the invention can reduce ghrelin output and thereby reduce appetite due to the bypass of the duodenum.

Type 2 diabetes is a disease of obesity that occurs when patients cannot adequately use the insulin they produce. Usually, it is not that the patient cannot make enough insulin, but rather that the patients body cannot effectively use the insulin produced. A particularly dangerous result of type 2 diabetes is that blood sugar spikes after a meal. This is called post-prandial hyperglycemia. This spike in blood glucose causes cardiovascular and microvascular damage. One class of drugs used to control post-prandial hyperglycemia is the alpha-glucosidase inhibitors. These work by reducing the breakdown and absorption of carbohydrates to sugars. The gastrointestinal device has a similar function because it reduces bile and delays the breakdown and absorption of the carbohydrates, which are normally readily absorbed in the duodenum, but are less likely to be absorbed in the jejunum and ileum. Therefore, type 2 diabetes can be controlled by placing a sleeve in the proximal intestine to delay the digestion of carbohydrates which reduces post-prandial hyperglycemia.

The gastrointestinal implant device can be used to reduce type 2 diabetes symptoms by bypassing all or a portion of the duodenum. Following gastric bypass surgery, patients commonly experience complete reversal of type 2 diabetes. While the exact mechanism of this remarkable effect is not understood, the clinical result is reported in a high percentage of cases. Since the gastrointestinal implant devices describe herein provides equivalent blockage of duodenal processes, a similar effect is elicited but without the trauma of surgery.

In the method of using the gastrointestinal device for treating diabetes, placement of the anchor within the stomach and/or duodenum allows the pylorus to operate normally. The length of the sleeve may be reduced to mimic the duodenum bypass. The sleeve may extends to just below the ligament of Treitz but may not extend further into the jejunum, thus allowing absorption to occur in the jejunum.

Other Embodiments

All publications, patents, and patent applications mentioned in this specification are herein incorporated by reference to the same extent as if each independent publication or patent application was specifically and individually indicated to be incorporated by reference. In the event of a conflicting definition between this and any reference incorporated herein, the definition provided herein applies.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure that come within known or customary practice within the art to which the disclosure pertains and may be applied to the essential features hereinbefore set forth, and follows in the scope of the claims.

Other embodiments are within the claims.

What is claimed is:

1. A gastrointestinal device comprising:
   (a) a sleeve configured to carry fluid from its proximal end to its distal end, wherein its proximal end is configured to be at or proximal to a subject's pyloric orifice and its distal end is configured to be at or distal to the subject's duodenum;
   (b) an anchor connected to the sleeve, the anchor configured to be retained within a duodenal bulb; and
   (c) a flange positioned proximal to the anchor, the flange configured to resist distal migration of the gastrointestinal device,
   wherein a coupling liner connects the anchor to the sleeve at a sleeve-coupling interface, wherein a relaxed diameter of the anchor is greater than a maximum diameter of the sleeve at the sleeve-coupling interface; or
   wherein the anchor is configured to exert an outward radial force on the sleeve at the sleeve-coupling interface, wherein the outward radial force on the sleeve at the sleeve-coupling interface is configured to maintain the sleeve in an open configuration at the sleeve-coupling interface, wherein the sleeve-coupling interface is at or distal to the distal-most end of the anchor or wherein the sleeve-coupling interface is from 1-6 inches distal to the flange.

2. The gastrointestinal device of claim 1, wherein the anchor is a wave anchor.

3. The gastrointestinal device of claim 2, further comprising a drawstring attached to the wave anchor, the drawstring configured to exert an inward radial force on a proximal end of the wave anchor when pulled proximally.

4. The gastrointestinal device of claim 1, wherein the flange is directly connected to the proximal end of the sleeve or the flange and the sleeve are made from a polymeric liner, wherein all or a portion of the sleeve is thinner than the polymeric liner of the flange.

5. The gastrointestinal device of claim 4, wherein the polymeric liner is selected from the group consisting of polytetrafluoroethylene (PTFE), expanded PTFE (ePTFE), fluorinated ethylene propylene (FEP), perfluoroalkoxy (PFA), ethylene tetrafluoroethylene (ETFE), and polyvinylidene fluoride (PVDF).

6. The gastrointestinal device of claim 1, wherein the flange is a circular flange having a maximum outer diameter that is at least 100% greater than a diameter of the sleeve.

7. A method of implanting the gastrointestinal device of claim 1, the method comprising attaching the flange to a proximally oriented luminal surface proximal to the pyloric orifice.

8. A method of treating a metabolic disorder, the method comprising implanting the gastrointestinal device of claim 1 by attaching the flange to a proximally oriented luminal surface proximal to the pyloric orifice.

9. The method of claim 8, wherein the metabolic disorder is type 2 diabetes or wherein the metabolic disorder is non-alcoholic steatohepatitis (NASH), non-alcoholic fatty liver disease (NAFLD), or obesity.

10. The method of claim 8, wherein the proximally oriented luminal surface is a proximal surface of the pyloric sphincter or an antral surface of a stomach.

11. The method of claim 8, wherein the attaching is performed endoscopically or comprises transmission of a distal force from an attachment element to the proximally oriented luminal surface.

12. The method of claim 11, wherein the attaching comprises puncturing a gastrointestinal wall.

13. The method of claim 11, wherein the attachment element comprises a suture or a staple.

14. A method of removing the gastrointestinal device of claim 1, the method comprising:
   (a) disengaging the flange from a proximally oriented luminal surface proximal to the pyloric orifice;
   (b) pulling a drawstring attached to the anchor, the drawstring configured to exert an inward radial force on a proximal portion of the anchor when pulled proximally; and
   (c) retracting the anchor into a retrieval catheter.

\* \* \* \* \*